United States Patent [19]

Kiso et al.

[11] Patent Number: 4,982,600

[45] Date of Patent: Jan. 8, 1991

[54] METHOD OF MEASURING THE PERIOD OF SURFACE DEFECTS

[75] Inventors: Takeshi Kiso, Kanagawa; Takanori Masuda, Shizuoka, both of Japan

[73] Assignee: Fuji Photo Film Co., Ltd., Kanagawa, Japan

[21] Appl. No.: 405,215

[22] Filed: Sep. 11, 1989

[30] Foreign Application Priority Data

Sep. 9, 1988 [JP] Japan .................. 63-226190

[51] Int. Cl.$^5$ .................................... G01B 21/30
[52] U.S. Cl. ................................... 73/104; 73/159
[58] Field of Search ................... 73/104, 105, 159

[56] References Cited

U.S. PATENT DOCUMENTS

| | | | |
|---|---|---|---|
| 2,950,436 | 8/1960 | Butticaz et al. | 73/159 X |
| 3,112,642 | 12/1963 | Harmon et al. | 73/105 |
| 3,377,828 | 4/1968 | Harmon | 73/105 X |
| 3,509,751 | 5/1970 | Shiraiwa et al. | 73/159 X |
| 3,544,774 | 12/1970 | Peklenik | 73/105 X |
| 3,633,211 | 1/1972 | Batzdorff | 377/16 X |
| 3,835,332 | 9/1974 | Bridges | 250/563 |
| 3,971,272 | 7/1976 | Felix et al. | 73/159 X |
| 4,048,849 | 9/1977 | Gocho et al. | 73/105 |
| 4,084,398 | 4/1978 | Stahlecker et al. | 57/81 X |
| 4,116,566 | 9/1978 | Sick | 350/6.7 X |
| 4,134,684 | 1/1979 | Jette | 250/563 X |
| 4,348,114 | 9/1982 | Neale et al. | 356/431 |
| 4,939,929 | 7/1990 | Östman | 73/159 |

FOREIGN PATENT DOCUMENTS

| | | | |
|---|---|---|---|
| 49-35091 | 4/1974 | Japan . | |
| 939929 | 6/1962 | U.S.S.R. | 73/105 |

Primary Examiner—Tom Noland
Attorney, Agent, or Firm—Young & Thompson

[57] ABSTRACT

To measure the period with which a surface defect recurs in a surface of a web-like material moving in its lengthwise direction, surface defects distributed over the surface are detected in that lengthwise direction. Positional data and distance data as to the detected surface defects relative to one another are collected for a predetermined length of the web-like material. The web-like material is determined to have a periodic surface defect appearing with a period between predetermined maximum and minimum periods when the distance data include a distance equivalent to an elemental period that is a whole-number multiple of a fundamental period.

3 Claims, 3 Drawing Sheets

METHOD OF MEASURING THE PERIOD OF SURFACE DEFECTS

BACKGROUND OF THE INVENTION

The present invention relates to a method of measuring the period with which a surface defect recurs along the length of a travelling web.

Various types of surface inspection apparatus for detecting surface defects of traveling webs, such as films, paper sheets, metal sheets, etc. are well known and widely used for quality control of the web.

Such a surface inspection apparatus is used to detect surface defects, such as scratches and pin holes, in a surface of a traveling web appearing not only at random but also periodically. Such periodic surface defect detection apparatus is known from, for example, Japanese Unexam. Patent Publ. No. 49-35091. According to such a periodic surface defect detection system, surface defects are counted by opening a time gate upon the lapse of a predetermined time period from the time the first surface defect is detected. After several repetitions of this periodic detection, if more than a predetermined number of surface defects are detected upon each periodic detection, the web is considered to have periodic surface defects.

In such periodic surface defect detection apparatus, because surface defects are counted for the predetermined time period starting at the time of a first detection of surface defect, if a surface defect that is detected first not a periodic surface defect, the period with which a surface defect appears periodically should be measured again. Therefore, it is hard to perform a real time measurement of the period with which a surface defect recurs in a surface of a web traveling along a web manufacturing line.

It has been proposed to perform the measurement of the period of recurrence of a surface defect in a real time manner by the use of an auto-correlation. To do this, a surface of a traveling web is divided into a plurality of data cells in the direction in which the web moves and each data cell is graded as defective or non-defective. The defective data cell is signified by a binary datum "1" and the non-defective data cell is signified by a binary datum "0". Then, the number of pairs of defects at a regular distance of j is calculated for a data row consisting of binary data for the number n of data cells by the use of the following auto-correlation:

$$AC(j) = \sum_{i=1}^{n-j} (d_i \cdot d_{i+j}) \quad (I)$$

wherein j is an integer from zero (0) to (n−1). In the auto-correlation I, $(d_i \cdot d_{i+j})$ is a product of a binary datum $d_i$ for an i-th data cell and a binary datum $d_{i+j}$ for a (i+j)-th data cell. That is, the product is "1" only when both of the binary data $d_i$ and $d_{i+j}$ are "1", indicating that both the i-th data cell and the (i+j)-th data cell are defective. Accordingly, the auto-correlation I expresses the number of pairs of defects at a regular distance of j for a data row consisting of binary data for the number n of data cells. Then, the following discrimination condition is used to determine the basic period of the surface defect:

$$AC(kf_o) > 0 \quad \text{II}$$

wherein k is an integer from 1 to l.

However, because of the necessity of calculating the auto-correlation I from all of the data, $d_i, d_2, \ldots, d_n$, the time required to perform the calculation is proportional to $n \cdot (n-1)$. That is, multiplication and addition have to be repeated $n \cdot (n-1)$ times for the number n of data. The number n is a value of the length L of the web undergoing testing divided by the unit length s.

The time necessary to perform the calculation of the period of a surface defect, which depends upon given hardware and program, has thus heretofore been long and a high processing capacity of the computer or special hardware is needed to perform such a calculation in an acceptably short time.

OBJECTS OF THE INVENTION

It is, therefore, an object of the present invention to provide a novel method of measuring the period of a surface defect in which an improved algorithmic auto-correlation is used to calculate the period of the defect.

It is another object of the present invention to provide a method of quickly measuring the period of a surface defect without using a large computer or specially provided hardware.

SUMMARY OF THE INVENTION

The objects of the present invention are achieved by providing a novel method of measuring the period with which a surface defect recurs in a surface of a web moving in its lengthwise direction. According to this novel method, surface defects distributed along the surface of the traveling web are detected during lengthwise movement of the weblike material, and positional data and distance data as to the plurality of surface defects relative to one another are collected for a predetermined length of the web. The web is determined to have a periodic surface defect having a period of recurrence between predetermined maximum and minimum periods, when the distance data include a distance equivalent to an elemental period that is a whole-number multiple of a fundamental period.

To detect surface defects, the surface of the traveling web is divided into a number of data cells and data as to each data cell are expressed by means of a binary datum "1" indicating a defective surface or a binary datum "0" indicating a non-defective or normal surface. After calculating the distances of correlative locations among the data cells having the defective surface datum "1", the periodicity of these surface defects is determined by the use of an autocorrelation expressing the frequency of appearance of these distances. In accordance with the present invention, the time needed to calculate the period of a surface defect is greatly shortened in comparison with a method using an autocorrelation resulting from performing a multiplication and an addition for all of the binary data. Therefore, the measurement of the period of a surface defect can be effected in an acceptably short time without using a large computer or specially provided hardware.

The collection of positional data is preferably effected every predetermined increment distance of movement of the web and the positional data of each surface defect are expressed in integer multiples of the predetermined incremental distance.

It is further preferred to measure the period of a surface defect for a plurality of lengthwise-extending lanes each having a predetermined width, into which the surface of the traveling web is divided.

DETAILED DESCRIPTION OF THE INVENTION

Figure 1:
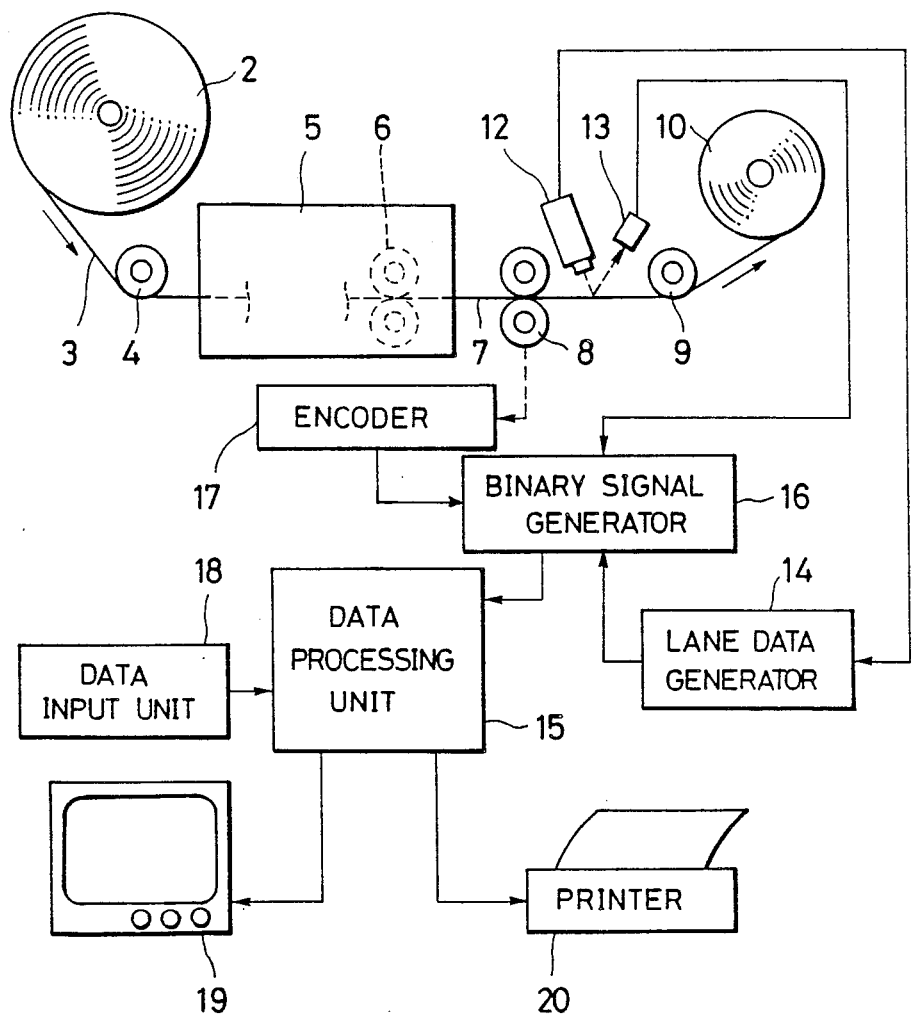
FIG. 1 is a schematic illustration showing a system for practicing the method of the present invention for measuring the period of a surface defect.

Referring to the drawings in detail, and in particular to FIG. 1, a method of measuring the period of a surface defect according to a preferred embodiment of the present invention which is applied to a lithographic plate manufacturing line is shown. An aluminum web 3 (which is hereinafter referred to as a base material) from which lithographic plates are made is rolled on a reel 2. The base material 3 is continuously withdrawn and transported toward a processing apparatus 5 by means of a drive roller 4. The processing apparatus 5 is provided with rollers 6 for polishing the surfaces of the base material 3 so as to make them smooth. The base material 7 thus smoothed is transported by means of drive rollers 8 and a guide roller 9 and wound around a reel 10.

A flying spot type of surface scanning device, which is disposed between the drive roller 8 and guide roller 9, consists of a scanner 12 and a light detector 13. The scanner 12 scans a surface of the base material 7 in a transverse direction perpendicular to the moving direction of the base material with a flying spot of small diameter. The light modulated by surface defects is reflected from the surface of the base material 7 and is directed toward the light detector 13. The light detector 13 detects the modulated light to provide a surface signal SS. As the scanner 12 scans the surface of the base material 7, detector 13 outputs surface signals SS to a lane data generator 14. The lane data generator 14 generates scanning lane signals SL indicating transverse positions or lanes of the surface of the base material 7 corresponding to the surface signals SS from the detector 13. The scanning lane signals SL are sent to a binary signal generator 16.

The light detector 13 extends in parallel to the transverse direction of the base material 7 to receive the light modulated by and reflected from surface defects of the base material 7. Accordingly, if the surface of the base material 7 has no surface defects, surface signals SS produced by the light detector 13 are at levels lower than a predetermined signal level. On the other hand, if the base material 7 has surface defects, the light detector 13 produces surface signals SS at levels greater than that predetermined signal level.

A rotary encoder 17 is connected to the drive roller 8 to produce scanning cell position signals SC indicating cells on the base material 7 in the moving direction and to send them to the binary signal generator 16.

The surface signals SS sent to the binary signal generating circuit 16 are converted to binary signals BS "0" or "1", according to their signal levels. That is, if a surface signal SS from the light detector 13 is at a signal level lower than the predetermined signal level, the binary signal generator 16 produces a binary signal BS of "0" indicating a standard or normal surface of the base material 7 (which is referred to as a standard surface) and if a surface signal SS from the light detector 13 is at a signal level greater than the predetermined signal level, the binary signal generator 16 produces a binary signal BS of "1" indicating a significant defect in the surface of the base material 7 (which is referred to as a defective surface). The binary signal BS is sent as a surface data signal to the data processing unit 15.

Data processing unit 15 is connected to a data input unit 18, such as a keyboard, through which various data are input to set the initial data necessary for measuring the period of a surface defect. The initial data and the result of measurement are displayed on a display 19, such as a CRT and, if desired, printed out by means of a printer 20. Display 19 and printer 20 can be of any well known type and need not be described in detail herein.

To measure the period of a surface defect in the base material 7, data are initially input to divide the surface of the base material 7 into a number of data cells by means of the data input unit 18. This determines the number of data cells of unit length s in the moving direction of the base material 7, as well as the number of lanes. Then, a length L of the base material 7 to be measured (which is referred to as a measuring length) is also initially set in accordance with the period of surface defects to be measured. It is to be noted in this embodiment that the measuring length L is set to be six times as long as the expected maximum period of surface defects.

After the initial setting, the surface scanning unit is actuated to scan the surface of the base material 7. Surface signals SS from the light detector 13 of the surface scanning unit are converted into binary signals BS (normal surface signals "0" or defective surface signals "1") which in turn are sent to the data processing unit 15.

Figure 2:
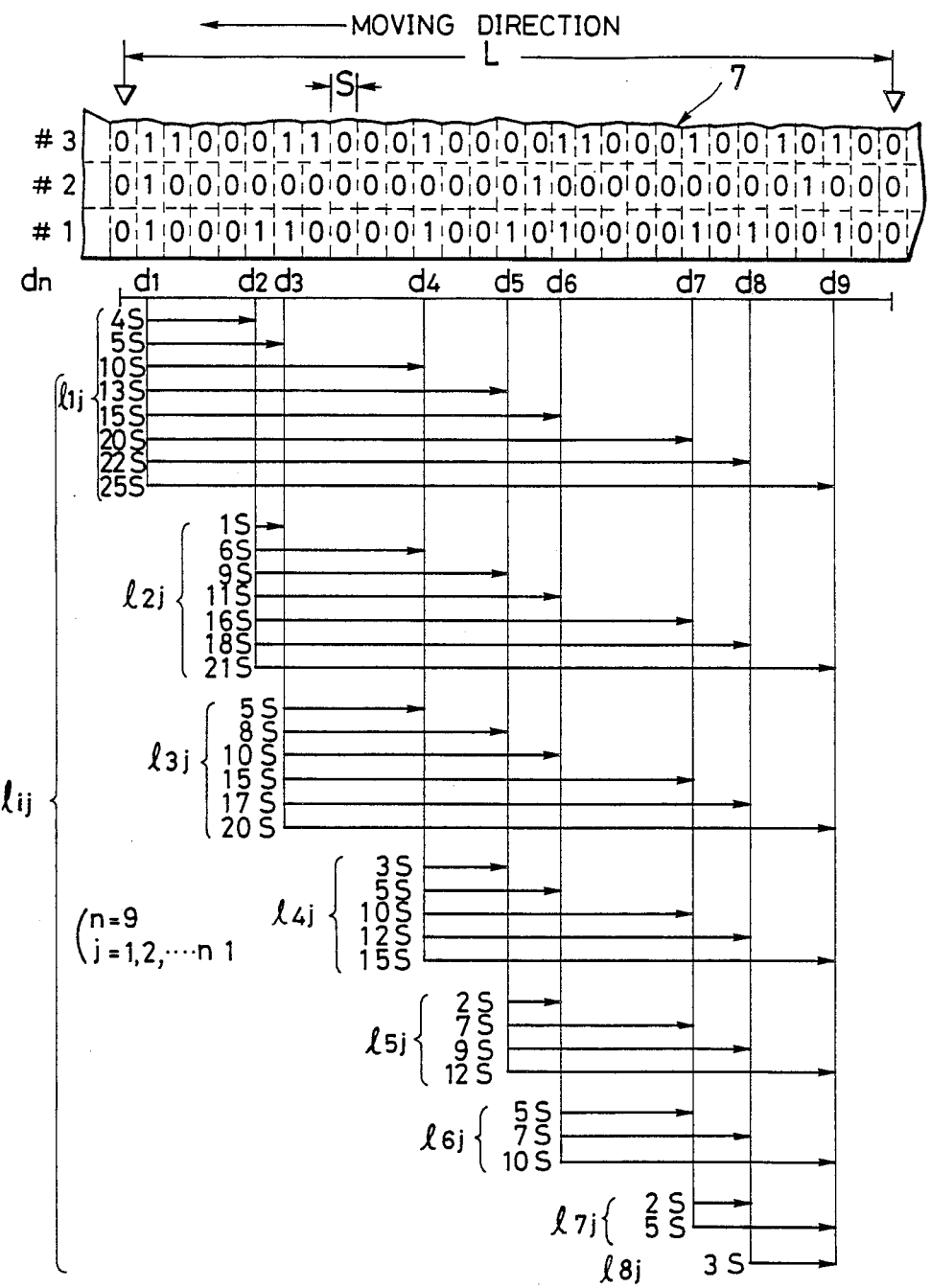
FIG. 2 is a schematic illustration showing an exemplary distribution of binary surface data and an autocorrelation obtained from the distribution of binary surface data.

Referring to FIG. 2 conceptionally showing a distribution of binary signals BS corresponding to data cells of the base material 7, the base material 7 of the measuring length L is divided into a number of lane, #1, #2, #3, . . . (three of which are shown in FIG. 2) in the transverse direction and each lane is divided into a number of, for example 29, data cells having a length equal to a unit distance s in the direction of the measuring length L. As shown, each data cell of the base material 7 is assigned one binary signal BS.

An example of measurement of the period of a surface defect in the first lane (#1) will be described with reference to FIG. 2. As is apparent from FIG. 2, there are a plurality m, for example 9, of defective surface signals "1" in the first lane (#1) along the measuring length L of the base material 7, which defective surface signals provide data as to the locations, in the moving direction, of the cells having surface defects. When assigning the respective defective surface signals "1" $d_1, d_2, \ldots, d_9$ in order of appearance from the left as viewed in FIG. 2, the distance $l_{ij}$ between every two defective surface signals "1", which must be integral multiples of the length of s of a data cell, can be obtained. An auto-correlation AC(ij), which indicates the period with which two defective surface signals "1" at a same distance $l_{ij}$ appear, is given in accordance with the obtained distances $l_{ij}$.

In the case of performing this measurement for the measuring length L of the base material 7 by the use of the auto-correlation $AC(l_{ij})$, a maximum time necessary to calculate the auto-correlation $AC(l_{ij})$ for the number m of defective surface signals "1" is proportional to m (m−1) and, therefore, is correlated to the number of defective surface signals. The maximum number of defective surface signals $M_{max}$ depends upon the minimum period of surface defect $X_{min}$ to be measured and is given as follows:

$$M_{max} = \text{Measuring Length } L/X_{min}$$

It is to be noted that the auto-correlation $AC(l_{ij})$ thus obtained is equivalent to the conventional auto-correlation $AC(j)$ as was previously described. The periodicity of this auto-correlation $AC(l_{ij})$ is discriminated by the following conditions:

$$AC(f_0) > 0, AC(2 \cdot f_0) > 0, \ldots, \text{ and } AC(1 \cdot f_0) > 0$$

where l is a preset multiplicative value for indicating a maximum elemental period $(1 \cdot f0)$ for discriminating the periodicity of the auto-correlation $AC(l_{ij})$ and is less than the number m.

These conditions are based on the fact that the elemental periods for the number m of periodic surface defects include a fundamental period $f_o$ and periods two to (m −1) times as long as the fundamental period $f_o$. According to these conditions, a fundamental period $f_o$ is obtained.

As described above, because the time necessary to calculate the auto-correlation $AC(l_{ij})$ is proportional to $m \cdot (m-1)$, the maximum time is proportional to $M_{max} \cdot (M_{max} - 1)$. Furthermore, because the maximum number $M_{max}$ of defective surface signals depends on the minimum period $X_{min}$ of surface defects and the minimum period $X_{min}$ is set approximately ten times as long as the unit distance s for adequate resolution in measurement, the maximum number $M_{max}$ of defective surface signals is expressed by using the total number of binary signals BS including normal surface and defective surface binary signals as follows:

$$M_{max} \leq \text{Measuring Length } (L)/10 \text{ Unit Distance}$$
$$(s) = n/10$$

In the case of the longest time necessary to calculate the elemental periods, a distance calculation (a subtraction of integers) and a frequency calculation (an addition of integers) are repeated $M_{max} \cdot (M_{max} - 1)$ times.

When using the conventional auto-correlation $AC(j)$, it is necessary to repeat a multiplication and an addition of binary signals $n \cdot (n-1)$ times. Although in both cases the time necessary to perform the calculation is different, depending upon the hardware and program in question, the ratio of total time necessary to calculate the auto-correlation $AC(l_{ij})$ in accordance with the present invention relative to the total time necessary to calculate the conventional auto-correlation $AC(j)$ period is expressed by the following expression, assuming that the time necessary to perform the calculation each time is the same in both cases:

$$M_{max} (M_{max} - 1)/[n \cdot (n - 1)] =$$
$$[n/10(n/10 - 1)]/n \cdot (n - 1) =$$
$$1/100 \cdot [(n - 10)/(n - 1)] \approx 1/100$$

It is to be noted that the number n of data cells will be sufficient if it is more than about 1,000, and can as a practical matter be about 3,333. When the number n is more than 1,000, the value of $(n-10)/(n-1)$ can be taken to be one (1).

Accordingly, although the time necessary for calculating the auto-correlation $AC(l_{ij})$ according to the present invention depends upon the number m of defective surface signals "1" included in the number n of binary signals BS, the use of the auto-correlation $AC(l_{ij})$ requires only about one hundredth of the total calculation time required by the conventional auto-correlation $AC(j)$ even in the case of the longest total calculation time.

Figure 3:
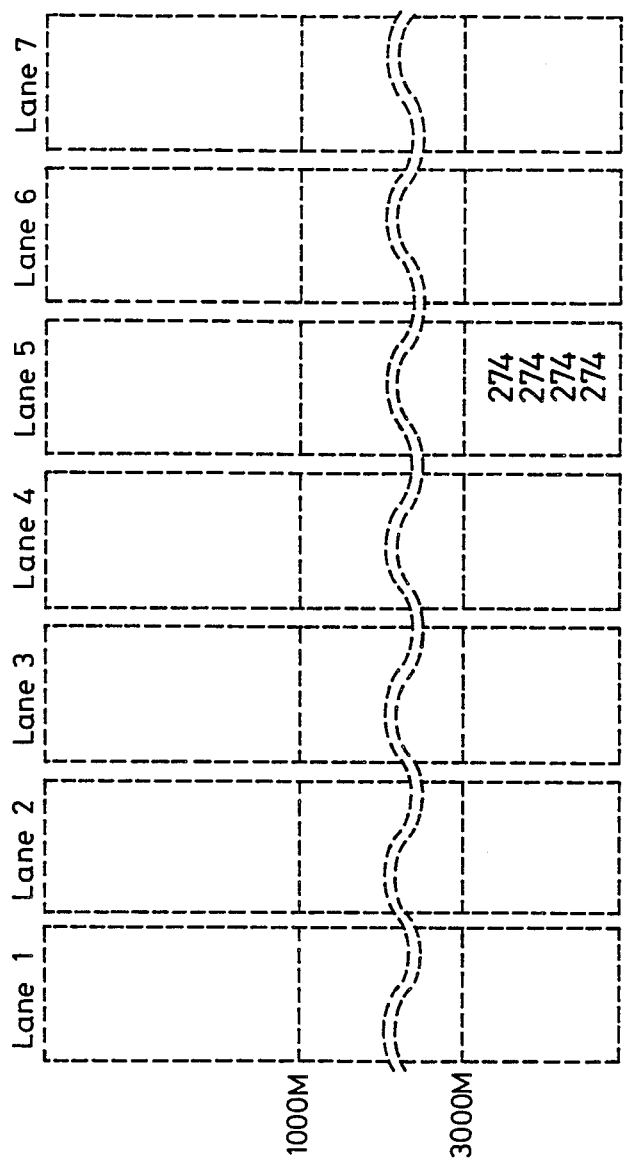
FIG. 3, is an illustration of output data as a result of measurement.

The display of data obtained from the detection of periodic surface defects is performed in the above-described manner. If periodic surface defects are detected, the printer 20 is actuated to print out data on the detected periodic surface defects as shown in FIG. 3. Let us take as an example a lithographic plate manufacturing line in which the present invention is embodied and in which the expected range of the periods of defects (minimum period $X_{min}$-maximum period $X_{max}$) and the unit distance s are set as 100–8,472 mm, and 15 mm, respectively. The base material 7, which usually has a maximum width of approximately 1,500 mm, is divided into 15 lanes each having a width of 100 mm so as to form data collecting areas of 15×100 mm on the base material 7. Accordingly, 15 bits of binary data are collected every 15 mm of movement of the base material 7.

In the example of printed data shown in FIG. 3, data on the first to seventh lanes of the base material 7 out of fifteen lanes are shown. Measurement of periodic surface defects is in practice performed for the fifteen lanes every 50 m of movement of the base material all at once. The maximum number of periodic surface defects is set to be 500. A sequence is programmed so as not to perform the calculation of the auto-correlation upon a decision of no periodicity of surface defects. The decision that there is no periodicity among these surface defects is made when more than 500 surface defects are detected in a measuring length of 50 m of the base material 7.

Although the measurement is effected every 50 m of advance of the base material 7, a measurement is output every 100 m of movement of the base material 7 as shown in FIG. 3. Because periodic surface defects of the base material 7 in the lithographic plate manufacturing line are often caused by surface irregularities of the rollers 4, 8, 9 and/or 6, the measurement result is, in the example shown in FIG. 3, numerically indicated by a value of a measured period of surface defect divided by the ratio of the circumference to the diameter of a roller. In FIG. 3, the indication "274" indicates that the base material 7 has a periodic surface defect caused by a roller having a diameter of 274 mm in the fifth lane (a region ranging from 400 to 500 mm from the side edge of the base material 7) at a distance of 3,000 to 3,400 m from the leading end of the base material 3.

Although the present invention has been fully described by way of a preferred embodiment thereof with reference to the accompanying drawings, it is to be noted that various changes and modifications will be apparent to those skilled in the art. Therefore, unless otherwise these changes and modifications depart from the scope of the present invention, they should be construed as being included therein

What is claimed is:

1. A method of measuring the period with which a defect in a surface of a web moving in a lengthwise direction thereof recurs, said method comprising the steps of:

moving a web relative to a scanning device to collect data on the positions of a plurality of said defects for a predetermined length of said web;

obtaining data on the distances of said plurality of defects from each other, and indicating that said web has a periodic defect recurring with a period between predetermined maximum and minimum periods when said distance data include a distance equivalent to an elemental period which is a whole-number multiple of a fundamental period.

2. A method as defined in claim 1, wherein said collection of positional data is effected every time said web moves said predetermined length and said positional data as to each said defect are expressed as a whole-number multiple of said predetermined length.

3. A method as defined in claim 2, wherein said measuring of the period of recurrence of a defect is effected for a plurality of lengthwise lanes having a predetermined width into which a surface of said web is divided.

* * * * *